United States Patent [19]

Ryan

[11] Plant 4,862

[45] Jun. 29, 1982

[54] IMPATIENS PLANT NAMED POMO

[76] Inventor: John J. Ryan, 39877 Sundale Dr., Fremont, Calif. 94538

[21] Appl. No.: 150,616

[22] Filed: May 16, 1980

[51] Int. Cl.[3] ..... A01H 5/00
[52] U.S. Cl. ..... Plt./68
[58] Field of Search ..... Plt./68

*Primary Examiner*—Robert E. Bagwill
*Attorney, Agent, or Firm*—James R. Cypher

[57] ABSTRACT

This invention relates to a new and distinct variety of New Guinea Impatiens plant, known by the cultivar name Pomo, a seedling resulting from the cross pollination of unpatented pollen parent 77-281-1 and unpatented pistil parent 77-310-1 and is distinguished by its many pink candy-striped flowers that seem to stay within the foliage canopy and a non-variegated foliage that can be described as chocolate colored, when grown under greenhouse conditions in Fremont, Calif.

3 Drawing Figures

BACKGROUND OF THE INVENTION

The present new variety (seedling) was discovered by me in a commercial greenhouse in Fremont, Calif., as a result of a definite breeding program to produce improved and different commercial varieties of impatiens plants.

The cross pollination of unpatented pistil parent 77-310-1 and unpatented pollen parent 77-281-1 produced the distinct new variety herein described and selected for propagation by cuttings. Repeated propagations and flowering of my new variety through asexual reproduction by terminal or stem cuttings grown in pots in a plastic (polyethylene) greenhouse in Fremont, Calif., under normal environmental conditions show that the characteristics described come true to form and are established and transmitted through succeeding generations.

BRIEF SUMMARY

The known commercial variety to which Pomo would be closest in characteristics is Chippewa, U.S. Plant Pat. No. 4,371 granted Jan. 23, 1979, but Pomo is distinctly different than Chippewa in the following outstanding characteristics:

1. Much more floriferous—both in number and earliness of flowering and does not flower in pulses as does Chippewa.
2. A darker green foliage with no variegation and more red pigmentation which can be described as chocolate colored when grown under greenhouse conditions in Fremont, Calif.
3. A darker pink candy-striped flower.
4. The flower has a shorter pedicel than Chippewa and doesn't extend beyond foliage in most cases.
5. Displays some marginal burn—suggesting that it is possibly sensitive to sodium as is U.S. Plant Pat. No. 4,194, granted Jan. 17, 1978, Hopi.

DESCRIPTION OF THE PHOTOGRAPH

The accompanying color photographs were taken at approximately 10 a.m. on Sept. 15, and 16, 1981, inside a commercial greenhouse having a cheese cloth roof on a sunny day in Fremont, Calif. Photograph A illustrates the overall appearance and form of the plant, as well as the shortness of pedicel that tends to hide the flower within the canopy of the foliage. Photograph B is a closeup view of the flower petals and foliage, and Photograph C is a photograph of a single blossom removed from the plant, and placed on a color strip taken from the Royal Horticultural Society Colour Chart packet that most closely describes the petal color. Applicant believes that photograph C depicts the true color of the petals.

DETAILED DESCRIPTION

Referring to the botanical details of my new variety, the following detailed description is based on observations made on Aug. 10, 1979 and on Sept. 15 and 16, 1981. All plants were grown under normal environmental conditions in greenhouses. Color readings were taken at approximately 1 p.m. in a greenhouse on a sunny day in Fremont, Calif., and all colors are based on the Royal Horticultural Society Colour Chart.

I. PLANT

Name: Pomo
Origin: Seedling of the cross pollination of the unpatented pistil parent 77-310-1 and the unpatented pollen parent 77-281-1.
Form: Upright spreading slightly.
Height to flowering: 30 cm.
Growth: Fast
Type of cutting: Terminal or stem.
Rooting time: Typical, 10–14 days.
Rooting habit: Fast, dendritic.

II. FOLIAGE

Arrangement: Lower leaves of any break are opposite; upper leaves of any break are whorls of 3 to 4.
Shape: Elliptical to oblanceolate.
Tip: Acuminate.
Base: Attenuate.
Margin: Serrulate.
Veination: Pinnate.
Size:
*Length of blade and petiole.*—11.0 cm to 15 cm.
*Length of blade.*—7.5 cm to 11.5 cm.
*Width of blade at widest point.*—2.5 cm to 4.0 cm.
Surface: Glabrous.
Variegation: None when grown in greenhouses at Fremont, Calif. However, Applicant is aware that when the plant is grown outdoors in California (Newark and Encinatas), some variegation does occur because of the greater amount of light received by the plant.

Color:

1. *Petiole.*—a. Upper 139D; b. Lower 53A.
2. *Veins.*—a. Upper 139D; b. Lower 53A.
3. *Leaf.*—a. Upper 147A; b. Lower 183B-C.

III. STEM

Color: 139D on older portion to 53A near apical meristem.

Internode:

1. *Length.*—Short to moderate.
2. *Size.*—Moderate. Node expanded (relative to internode); slightly expanded.

Breaking action: Moderate.

IV. FLOWER

Form: Typical

Borne: End of branches, terminal, shorter pedicels

Blooming habit:

1. *Relative number.*—Many.
2. *Time to flowering.*—Short.
3. *Longevity.*—4–7 days, little longer than most.

Size of mature flower: First flower on a plant usually is small.

1. *Length.*—5.5 cm to 6.0 cm.
2. *Width.*—5.5 cm to 6.0 cm.
3. *Spur.*—5.0 cm to 5.5 cm.

Color:

1. *Eye.*—57B (young) to 57D (old flower).
2. *Middle.*—39B-C (young) to 39C-D (old flower).
3. *Edge.*—40B.

4. *Candy-striped.*—40B-C (young) to 39B-C (old flower).
5. *Pedicel.*—145A-B.

V. REPRODUCTIVE ORGANS

Stamen:

| | |
|---|---|
| 1. *Anthers*<br>2. *Filaments* | Typical, fused hood over pistil. |
| 3. *Pollen*—a. | Color-158B; b. Abundance-less than average. |

Pistils:

| | |
|---|---|
| 1. *Style*<br>2. *Ovaries* | Typical but colored 187A—top of ovary just under stigma. |

VI. OTHER CHARACTERISTICS

Pomo displays some marginal burn, suggesting that it is possibly sensitive to sodium as is U.S. Plant Pat. No. 4,194, Hopi.

I claim:

1. A new and distinct form of Impatiens plant as described and illustrated, known by the cultivar name Pomo.

* * * * *

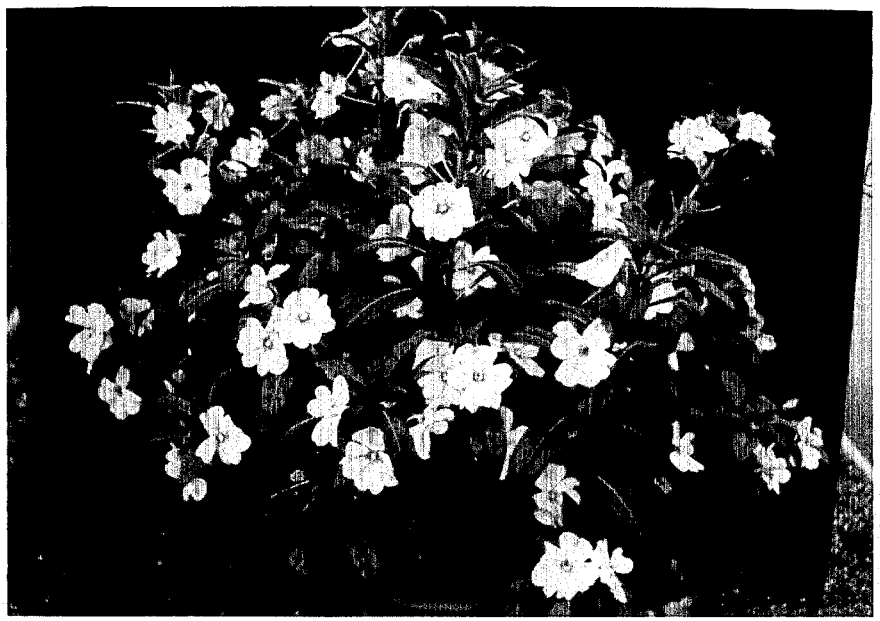
A
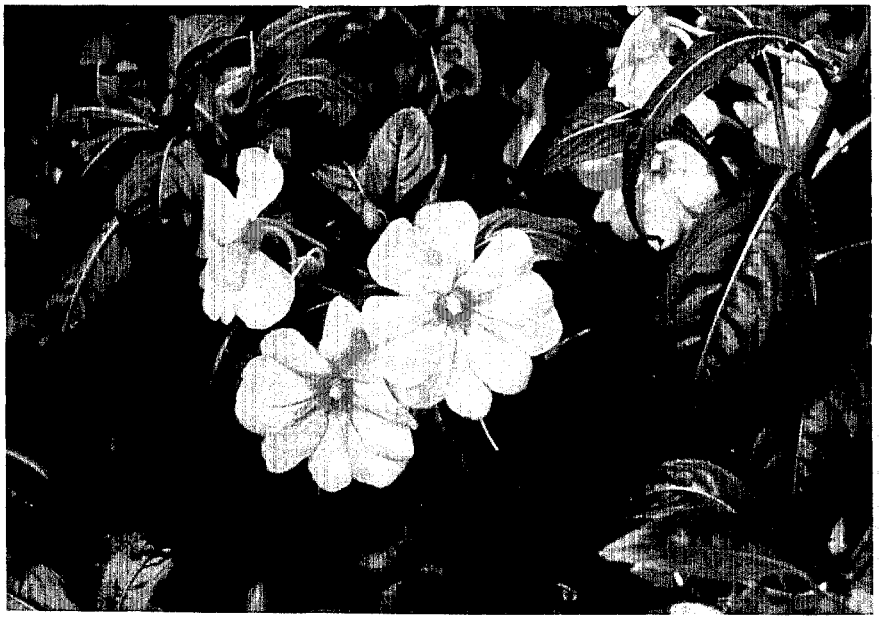
B

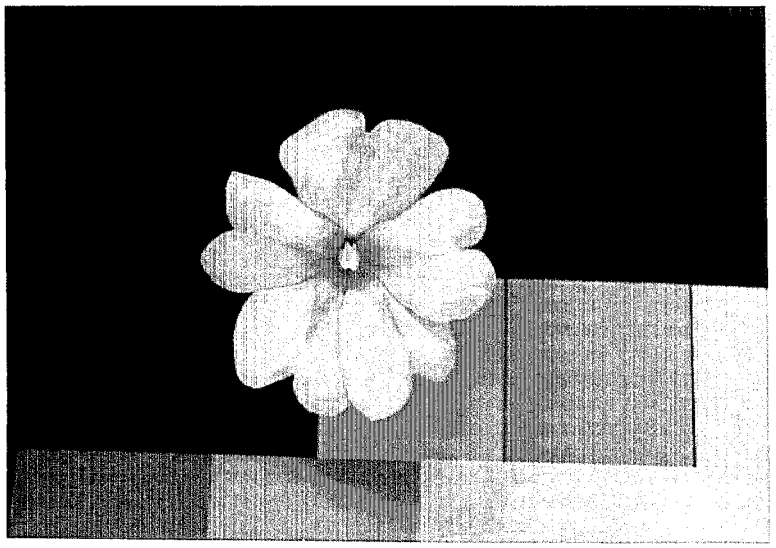
C